US010393674B1

(12) United States Patent
Lenchner et al.

(10) Patent No.: US 10,393,674 B1
(45) Date of Patent: Aug. 27, 2019

(54) INFRARED-BASED APPARATUS FOR DETECTING GAPS IN MOSQUITO NETTING

(71) Applicant: INTERNATIONAL BUSINESS MACHINES CORPORATION, Armonk, NY (US)

(72) Inventors: Jonathan Lenchner, Nairobi (KE); Aisha Walcott, Nairobi (KE); Charles Muchiri Wachira, Nairobi (KE); Samuel Osebe, Ongata Rongai (KE); Sekou L. Remy, Nairobi (KE); Stephen Oduor Odhiambo, Nairobi (KE)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 16/155,185

(22) Filed: Oct. 9, 2018

(51) Int. Cl.
*G01N 21/35* (2014.01)
*G01N 21/95* (2006.01)
*G01N 21/956* (2006.01)
*G01N 21/3563* (2014.01)

(52) U.S. Cl.
CPC ... *G01N 21/95692* (2013.01); *G01N 21/3563* (2013.01)

(58) Field of Classification Search
CPC .............. G01N 21/3563; G01N 21/95692
See application file for complete search history.

(56) References Cited

U.S. PATENT DOCUMENTS 3,841,761 A 10/1974 Selign
5,150,175 A 9/1992 Whitman et al.
5,283,623 A 2/1994 Muhlberg et al.
5,575,105 A 11/1996 Otomo
9,476,159 B2 * 10/2016 France ............... D06H 3/08

FOREIGN PATENT DOCUMENTS

CN 202386281 U 8/2012
CN 105844847 A 8/2016
DE 202004002675 U1 4/2004

OTHER PUBLICATIONS

Eng, "Assessing Bed Net Damage: Comparisons of three Measurement Methods for Estimating the Size, Shape, and Distribution Holes on Bed Nets", Malaria Journal (Oct. 2017) pp. 1-13.
Sutcliffe, "Video Studies of Passage by Anopheles Gambiae Mosquitoes Through Holes in a Simulated Bed Net: Effects of Hole Size, Hole Orientation and Net Environment", Malaria Journal (May 2015) pp. 1-13.

* cited by examiner

*Primary Examiner* — Mark R Gaworecki
(74) *Attorney, Agent, or Firm* — Tutunjian & Bitetto, P.C.; Eyal Gilboa

(57) ABSTRACT

Systems and methods for detecting gaps in netting include constructing a depth map from electromagnetic signals associated with netting surrounding an area, the depth map including measurements of distance of each strand of the netting along an axis perpendicular to a plane formed by the netting relative to the detector. Each segment of netting is identified including each strand of the netting in a side of the netting facing the detector. Locations of gaps in the netting are identified according to the depth map. A user is alerted to the presence and locations of gaps by sending a communication to a computing device.

20 Claims, 7 Drawing Sheets

> Identify depth-wise gaps in the netting by identifying first strands of netting having a depth greater than second strands of netting at a same horizontal and vertical location
> 507

> Identify a portion of the IR image depicting more than one layer of netting according to at least one strand having a depth measurement different by greater than a threshold from a depth measurement of at least one other strand within a radius of each other in the IR image
> 601

> Determine that the more than one layer are separate segments of netting separated by a depth-wise gap by tracing the one or more strands in the portion from end to end to determine that the at least one strand and the at least one other strand are not connected
> 602

FIG. 6

INFRARED-BASED APPARATUS FOR DETECTING GAPS IN MOSQUITO NETTING

BACKGROUND

Technical Field

The present invention generally relates to infrared pattern detection, and more particularly to an infrared-based apparatus for detecting gaps in mosquito netting.

Description of the Related Art

Mosquito borne illnesses, such as malaria, affect a large amount of people, particularly in tropical regions. For many of these illnesses, medical treatments are expensive, ineffective, or otherwise infeasible for preventing the spread and contraction of these illnesses. However, some steps can be taken to prevent mosquito bites, and thus reduce the risks of contracting a mosquito borne illness. For example, mosquito netting, particularly insecticide treated mosquito netting, hung around a bed is an effective method of preventing mosquito borne illness while sleeping.

However, to effectively prevent mosquito bites, mosquito netting cannot have any openings large enough for a mosquito to penetrate. Thus, any gaps in the mosquito netting can result in a high risk of mosquito bites and thus contracting a mosquito borne illness.

SUMMARY

In accordance with an embodiment of the present invention, a method for detecting gaps in netting is described. The method includes constructing a depth map from electromagnetic signals associated with netting surrounding an area, the depth map including measurements of the distance of each strand of netting from the detector. Each segment of netting is identified including each strand of the netting in a side of the netting facing the detector. Locations of gaps in the netting are identified according to the depth map. A user is alerted to the presence and locations of gaps by sending a communication to a computing device.

In accordance with another embodiment of the present invention, a system for detecting gaps in netting is described. The system includes an electromagnetic detector that captures an electromagnetic signal from netting surrounding an area, the electromagnetic signal including a signal and an angle of the signal from each strand of the netting. A signal processor includes a memory device and a processor to process the captured electromagnetic signal. The signal processor includes a depth mapper that constructs a depth map from the signals, the depth map including measurements of distance of each strand of the netting from the detector, a pattern recognition engine that identifies the netting, and a gap locator that identifies locations of gaps in the netting according to the depth map of the netting. A notifier alerts a user to the presence and locations of gaps.

In accordance with another embodiment of the present invention, a non-transitory computer readable storage medium comprising a computer readable program for detecting gaps in netting is described. The computer readable program when executed on a computer causes the computer to perform the steps of constructing a depth map from electromagnetic signals associated with netting surrounding an area, the depth map including measurements of distance of each strand of the netting from the detector. Each segment of netting is identified including each strand of the netting in a side of the netting facing the detector. Locations of gaps in the netting are identified according to the depth map. A user is alerted to the presence and locations of gaps by sending a communication to a computing device.

These and other features and advantages will become apparent from the following detailed description of illustrative embodiments thereof, which is to be read in connection with the accompanying drawings.

BRIEF DESCRIPTION OF THE DRAWINGS

The following description will provide details of preferred embodiments with reference to the following figures wherein:

FIG. 6 is a block/flow diagram showing a system/method detecting and identifying depth-wise gaps in netting, in accordance with an embodiment of the present invention.

DETAILED DESCRIPTION

Figure 1:
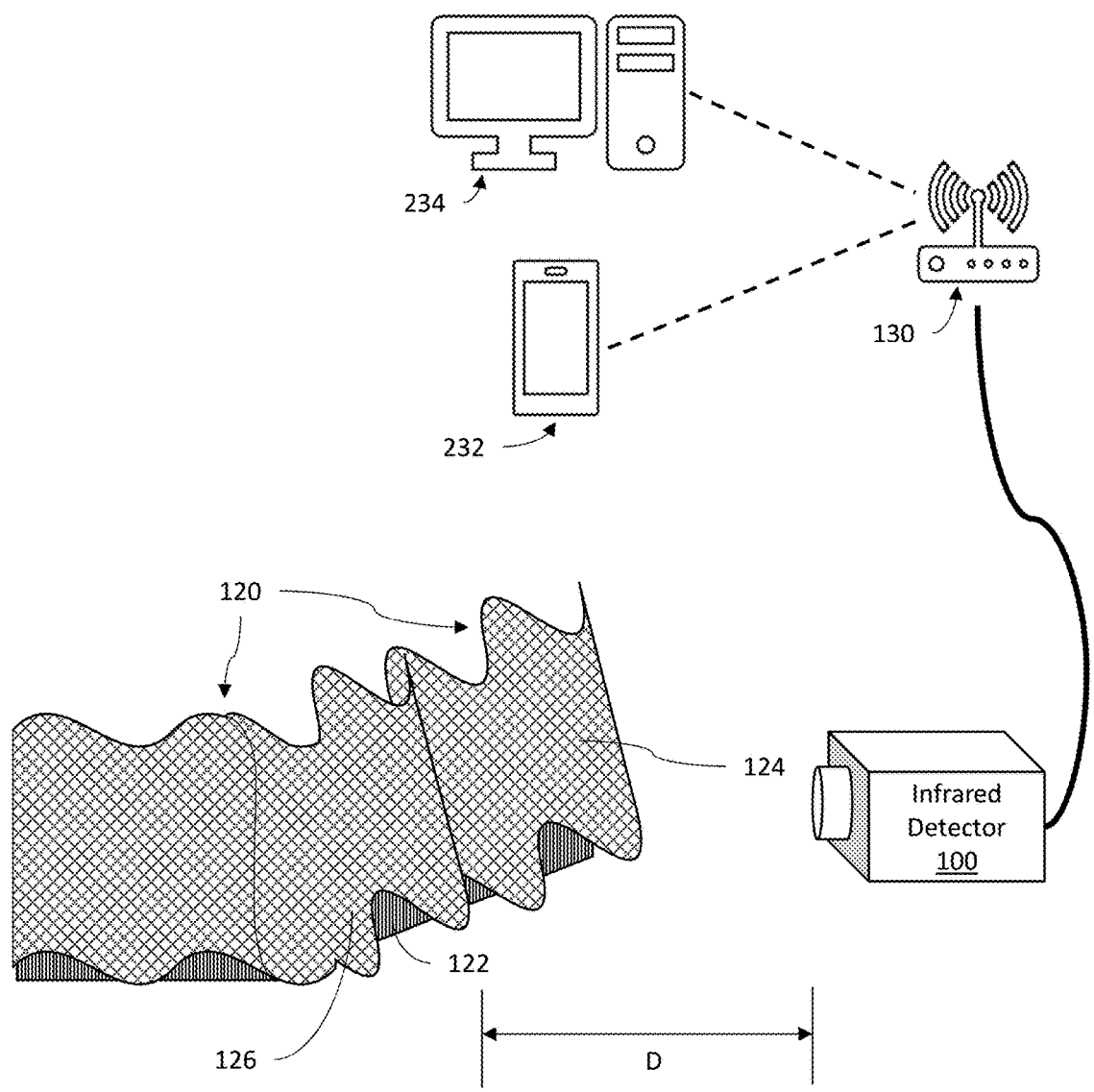
FIG. 1 is a diagram showing a system for gap detection in netting, in accordance with an embodiment of the present invention.

According to an embodiment of the present invention, a system and method for detecting gaps in mosquito netting are contemplated that utilize electromagnetic (EM) sensors to detect irregularities in the netting.

In one possible embodiment of the present invention, the EM sensors include infrared (IR) sensors to detect IR signals. The IR sensors can be positioned in one or more locations around an area bounded by the netting, such as, e.g., around a bed. Each IR sensor can use IR imaging to sense a portion of the netting on a side of the area. For example, an IR sensor can project an IR signal towards the netting and analyze the reflected infrared signal. Every object radiates and reflects a characteristic amount of infrared radiation according to the shape, size, and molecular make-up of the objects. Thus, each object, including, e.g., the netting, furniture, sheets and blankets, among other objects in and around the area, can be fingerprinted with the spectrum and the geometry of the reflection of the IR signal. For example, the netting reflects the IR signal by reflecting the signal striking the individual strands of the netting, thus reflecting a grid shaped IR reflection pattern having a spectral signature in accordance with the material of the netting.

A depth map can be created from images captured by the IR sensor according to the reflected IR signal. Distances from the IR sensor to each object in and around the area can be determined by, e.g., using an angle of the sensed IR signal, using a parallax effect due to stereoscopic detection of the IR signal, incorporating patterned infrared sensing, among other depth sensing techniques. Thus, the depth of each strand of the netting, as well as each other object, can be determined. Using the depths, any depth-wise gaps in the netting can be determined. In particular, in portions of the depth map where two netting layers are detected, overlapping with respect to the IR sensor, a distance of each netting layer is determined. One or more strands of one of the netting layers is then traced until an end of the strand is reached. If the strand traverses both layers of the netting, then the two layers are the result of a wrinkle in the netting and a depth-wise gap does not exist. However, if the strand does not traverse both layers, then a depth-wise gap does exist.

Moreover, the depth map includes vertical and horizontal positions of each object including, e.g., each strand of the netting, where the vertical and horizontal directions are perpendicular to the depth direction, or parallel to a plane of the netting on a particular side of the area being bounded. Thus, a portion of the depth map where a space exists between netting strands that is larger than the size of a mosquito, then an x/y gap exists between segments of netting.

Upon identifying gaps in the netting, a user is notified. The notification is one or both of directing a visible beam towards the location of the gap, and sending a message to the user's phone. Thus, the user can be notified of a gap that might let a mosquito through thereby increasing the risk of contracting a mosquito borne illness.

Exemplary applications/uses to which the present invention can be applied include, but are not limited to: identifying gaps in mosquito netting, fishing nets, transparent or semi-transparent fabrics, among other materials.

Referring now to the drawings in which like numerals represent the same or similar elements and initially to FIG. 1, a diagram of a system for gap detection in netting is shown in accordance with an embodiment of the present invention.

According to an embodiment of the present invention, a bed 122 is bounded by netting 120 having at least a first netting segment 124 and a second netting segment 126. The netting 120 can have any number of sides to bound an area such as the bed 122. Thus, the netting 120 can form a perimeter in the shape of, e.g., a rectangle or other polygon, or a circle or ellipse, or any other shape to bound the area.

The first netting segment 124 and the second netting segment 126 can be on a same side of the bed 122. The two segments of netting 120 can be used to open a gap between the first netting segment 124 and the second netting segment 126 to permit entry into the bed 122 area. However, to prevent mosquito entry, the two segments are brought back into an overlapping arrangement with each other. Sometimes, closing the gap in this manner is not fully effective and one or more gaps between the first netting segment 124 and the second netting segment 126 may remain. These gaps are potential entry points for mosquitoes. Similarly, holes and tears may develop in one or more segments of netting 120, opening gaps which also can provide an entry point for mosquitoes. Each of these gaps can be detected using an infrared detector 100.

The infrared detector 100 detects an infrared (IR) signal from objects in the vicinity of the bed 122 and netting 124 and 126. The infrared detector 100 uses the IR signal to inspect a portion of the netting 120 including the first netting segment 124 and the second netting segment 126, and a seam or overlapping region of the first and second netting segments 124 and 126. Depending on the size of each segment and the size of the netting 120 in general, as well as the number of sides of the bounded area, multiple infrared detectors 100 can be used such that the entirety of the netting 120 can be inspected. Alternatively, infrared detectors 100 can be positioned to only inspect the sides of the bounded area that are adjacent to an open area. For example, infrared detectors 100 may not be needed for a side of a bed pushed up against a wall because the risk of a gap being opened on the side of the wall is low or negligible. Thus, infrared detectors 100 would be positioned to only view the sides of the bed 122 that are not adjacent to walls.

The use of IR facilitates depth measurements, however, other portions of the electromagnetic spectrum can be used to inspect the netting 120, such as, e.g., ultraviolet (UV), visible light, or any other suitable range of the electromagnetic spectrum. Thus, the infrared detector 100 captures both an image of the first netting segment 124, the second netting segment 126 and the bed 122, as well as depth information of each object present within an area of detection according to a field of view of the infrared detector 100. The infrared detector 100 can use, e.g., an IR emitter placed at a predetermined offset from the infrared detector 100 to determine an angle of IR reflection off each object, and thus determine a depth of each object. Alternatively, two infrared detectors 100 can be used in conjunction at a pre-determined offset from each other such that the parallax of the IR images captured by each detector can be used to determine an angle, and thus a depth, of the IR signal from each object, similar to stereoscopic vision.

The depth information can be used to form a depth map that presents depth information for strands of each of the first netting segment 124 and the second netting segment 126 as well as any objects behind each netting segment such as the bed 122. The depth information can include, e.g., a measurement of distance D from the infrared detector 100, or a variation from a pre-established distance D between the infrared detector 100 and, e.g., the bed 122. For example, the depth measurement can be determined as a difference between the pre-established distance D and a measured distance between the infrared detector 100 and one or both of the first netting segment 124 and the second netting segment 126. However, the depth information can also include relative positioning without a precise measurement, for example, a depiction or representation that, e.g., the second netting segment 126 is in front of the first netting segment 124, and both of the first netting segment 124 and the second netting segment 126 are in front of the bed 122. Because the netting 120 has holes between strands, objects such as a bed 122 and a segment of the netting 120 can be seen through another segment of the netting 120. Thus, the depth map can include the netting 120 as well as depth information for anything behind the netting 120, including additional netting 120.

The depth map can be assessed for any gaps in the netting 120, including the first netting segment 124 and the second netting segment 126. Gaps can include a separation at a seam between the first netting segment 124 and the second netting segment 126, the separation being either in a depth-wise direction with respect to depth D (e.g., a z-direction), or in a direction perpendicular to depth D (e.g., an x-direction or y-direction), or a combination thereof. Gaps can also include holes or tears in the netting 120. The assessing can include determining differences in depth between one layer of netting 120 and a second layer of netting 120 to determine that there are overlapping layers of netting 120 with respect to the perspective of the infrared detector 100. Such an overlap can include a z-direction, or depth-wise, gap between the layers where there is a depth-wise separation between the two layers of the netting 120. The x-direction and y-direction gaps can be assessed by identifying the edges of the both the first netting segment 124 and the second netting segment 126 and identifying a space between strands of the first and/or second netting segment 124 and 126 is, e.g., large enough for a mosquito to fit through. Such identification can include, e.g., measuring a distance between adjacent strands and comparing the measurement to a threshold value representative of the size of a mosquito.

The results of the depth map assessment can be communicated to a transmitter 130 to communicate information regarding a gap to a user device. The transmitter 130 can include, e.g., a wireless transmitter such as, e.g., a Wi-Fi transmitter, a Bluetooth transmitter, a radio frequency (RF) transmitter, a cellular network transmitter, or a wired transmitter such as, e.g., an ethernet connection, an optical fiber transmitter, or any other data communication device.

The transmitter 130 sends an alert to a user device concerning the identified gaps in the netting 120 so that the gaps can be closed. The user device can include, e.g., a smartphone 232 or other text enabled phone, a computer 234, or any other device suitable for receiving a message by text, audio, video, images or other format. The alert can include a notice that a gap exists. Additionally, the alert can include, e.g., information regarding the location of the gap, the size of the gap, the type of gap (e.g., separation between netting 120 segments, tear, hole, separation between the netting 120 and a floor, or any other type of gap), as well as any other information.

Alternatively, the transmitter 130 can be a stand-alone alert device or notifier. Rather than communicating the alert to another device electronically, the transmitter 130 can produce a notification to alert the user via, e.g., a speaker, indicator light, display, or other user perceptible means of alert from the transmitter 130 itself.

Figure 2:
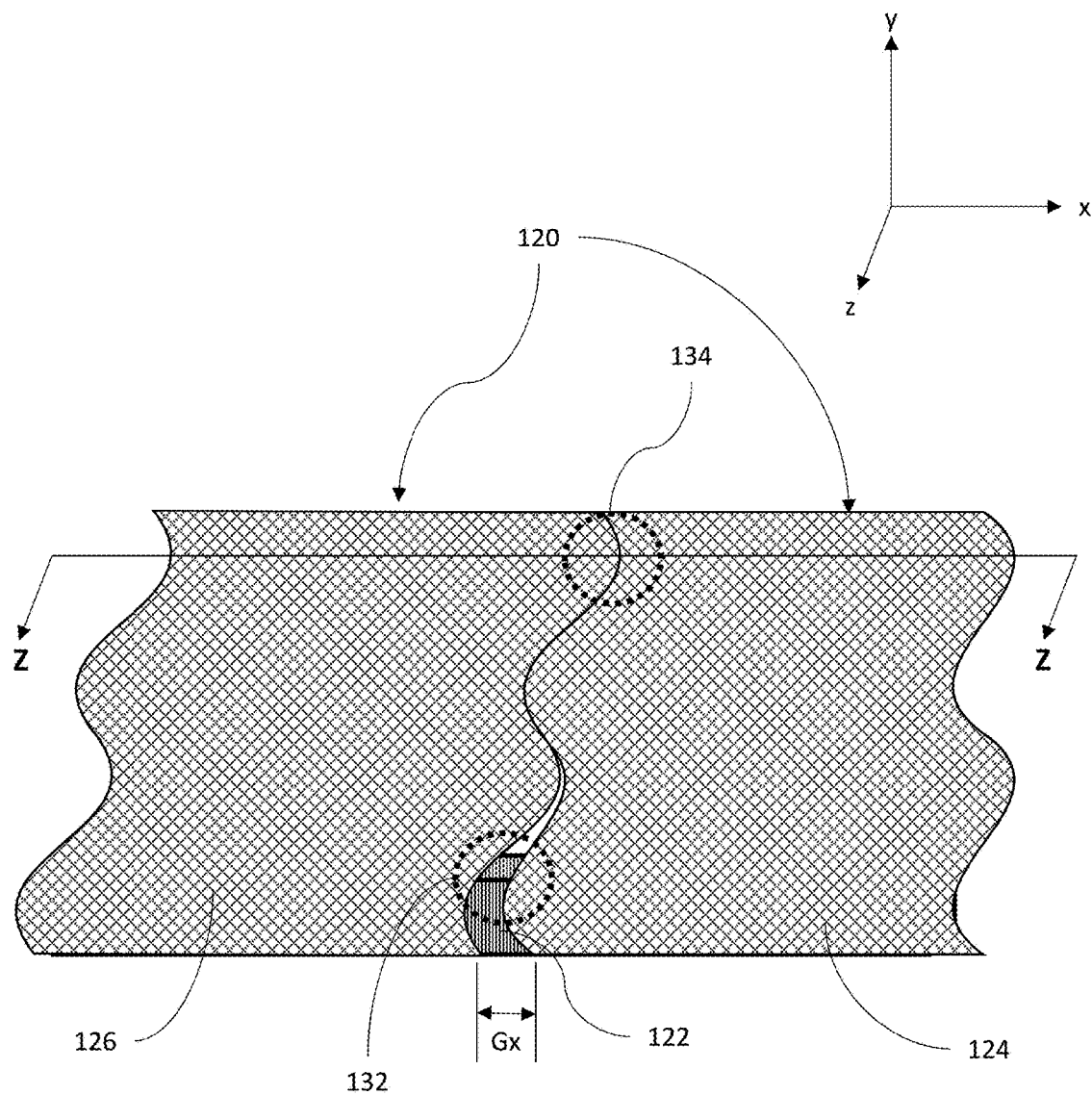
FIG. 2 is a diagram illustrating types of gaps in netting, in accordance with an embodiment of the present invention.

Referring now to FIG. 2, a diagram of types of gaps in netting is shown in accordance with an embodiment of the present invention.

As described above, the netting 120 can include two or more segments, such as, e.g., a first netting segment 124 and a second netting segment 126. While the first netting segment 124 and the second netting segment 126 can be connected at another location, the first netting segment 124 and the second netting segment 126 have ends that do not connect. Thus, an opening can be made between the first netting segment 124 and the second netting segment 126 such that a person can enter or exit a bounded area such as a bed 122. At this area of separation, when the first netting segment 124 and the second netting segment 126 are brought together to close the opening, gap 132, with corresponding net opening edge 134, can form due to inadequate closure of the opening.

According to aspects of the present invention, at least two types of gaps can be identified in the netting 120. The gaps can be in any of the x-, y- or z-directions as indicated by the coordinate axes. The x-direction is a horizontal direction perpendicular to the axis of the view of the infrared detector. Similarly, the y-direction is perpendicular to the axis of the view of the infrared detector, only in a vertical direction relative to the axis. The z-direction is parallel to the axis of the view of the infrared detector. Thus, the z-direction is related to the depth in a depth map generated by the infrared detector and is related to a distance from the infrared detector.

Therefore, the first gap 132 is an illustration of a gap in the x-direction relative to a view from an infrared detector, such as, e.g. the infrared detector 100 described above. The first gap 132 can occur, e.g., due to improper closing of an opening between the first netting segment 124 and the second netting segment 126. The first gap 132 can be measured in width to have a gap size of Gx. Where Gx is greater than a threshold amount, such as, e.g., greater than a size of a mosquito, the first gap 132 can be identified as a risk of permitting entry of mosquitoes.

The second gap 134 can be, e.g., a depth-wise gap in the z-direction. Thus, even though the ends of each of the first netting segment 124 and the second netting segment 126 extend past each other, the opening may still be present due to improper closing the in the z-direction. Similar to the first gap 132, the second gap 134 can be identified as a risk of permitting the entry of mosquitoes.

Figure 3:
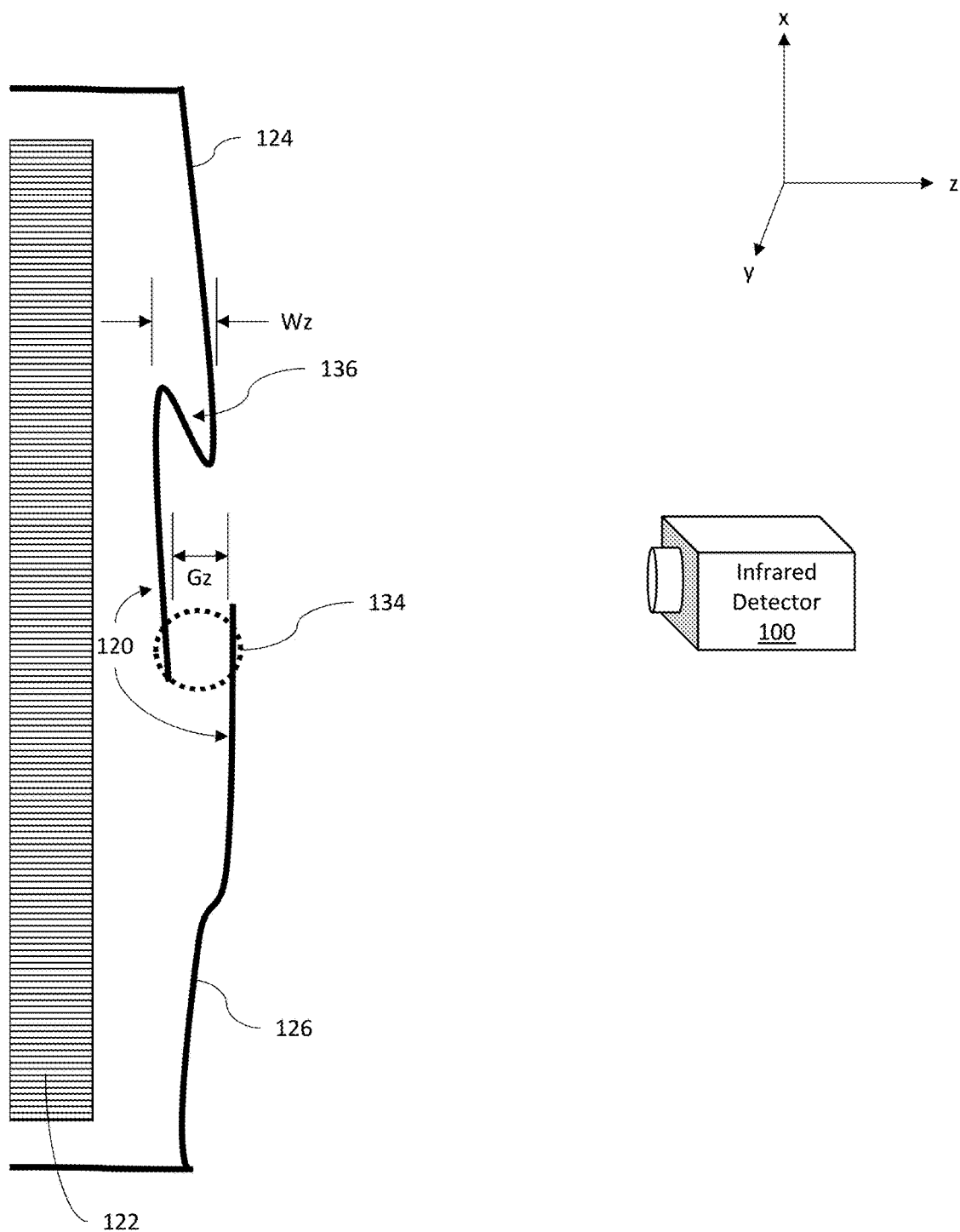
FIG. 3 is a top view from cross-section Z-Z of FIG. 2 illustrating the detection of types of gaps in netting, in accordance with an embodiment of the present invention.

Referring now to FIG. 3, a top view from cross-section Z-Z of FIG. 2 is illustrating showing the detection of types of gaps in netting in accordance with an embodiment of the present invention.

This second gap 134 can be a z-direction, or depth-wise gap relative to the infrared detector 100. Thus, the second gap 134 can include a depth-wise separation of the first netting segment 124 behind the second netting segment 126 of Gz. Because the second netting segment 126 has strands with holes between the strands, the second netting segment 126 is, in effect, semi-transparent. Thus, the infrared detector 100 can detect an infrared signal of the strands to the first netting segment 124 through the holes of the second netting segment 126. As a result, a depth of the strands of the first netting segment 124 and the second netting segment 126 can be compared to determine the size of Gz. If Gz is greater than a threshold amount, such as, e.g., the size of a mosquito, the second gap 134 can be identified as a risk of permitting mosquito entry.

However, there can be multiple layers of netting 120 that do not include depth-wise gaps, such as, e.g., wrinkle 136. The wrinkle 136 in the first netting segment 124 has three layers of netting 120 which the infrared detector 100 can detect as described above in reference to the second gap 134. However, the layers of netting 120 are a result of the netting 120 of the first netting segment 124 folding over on itself. The infrared detector 100 can identify the wrinkle 136 as a folding of the netting 120 by, e.g., tracing a strand of the first netting segment 124 that passes through the area of the wrinkle 136 in the x-direction and y-direction. By tracing the strand through the area of the wrinkle 136, the infrared detector 100 can determine if the strand passes through the area in each layer of the wrinkle 136, or if the strand ends before passing the area in another layer. In the event that the strand does pass through the wrinkle 136 more than once, then the wrinkle 136 can be identified as a wrinkle or fold in the first netting segment 124 to produce the multiple layers of the netting 120.

Figure 4:
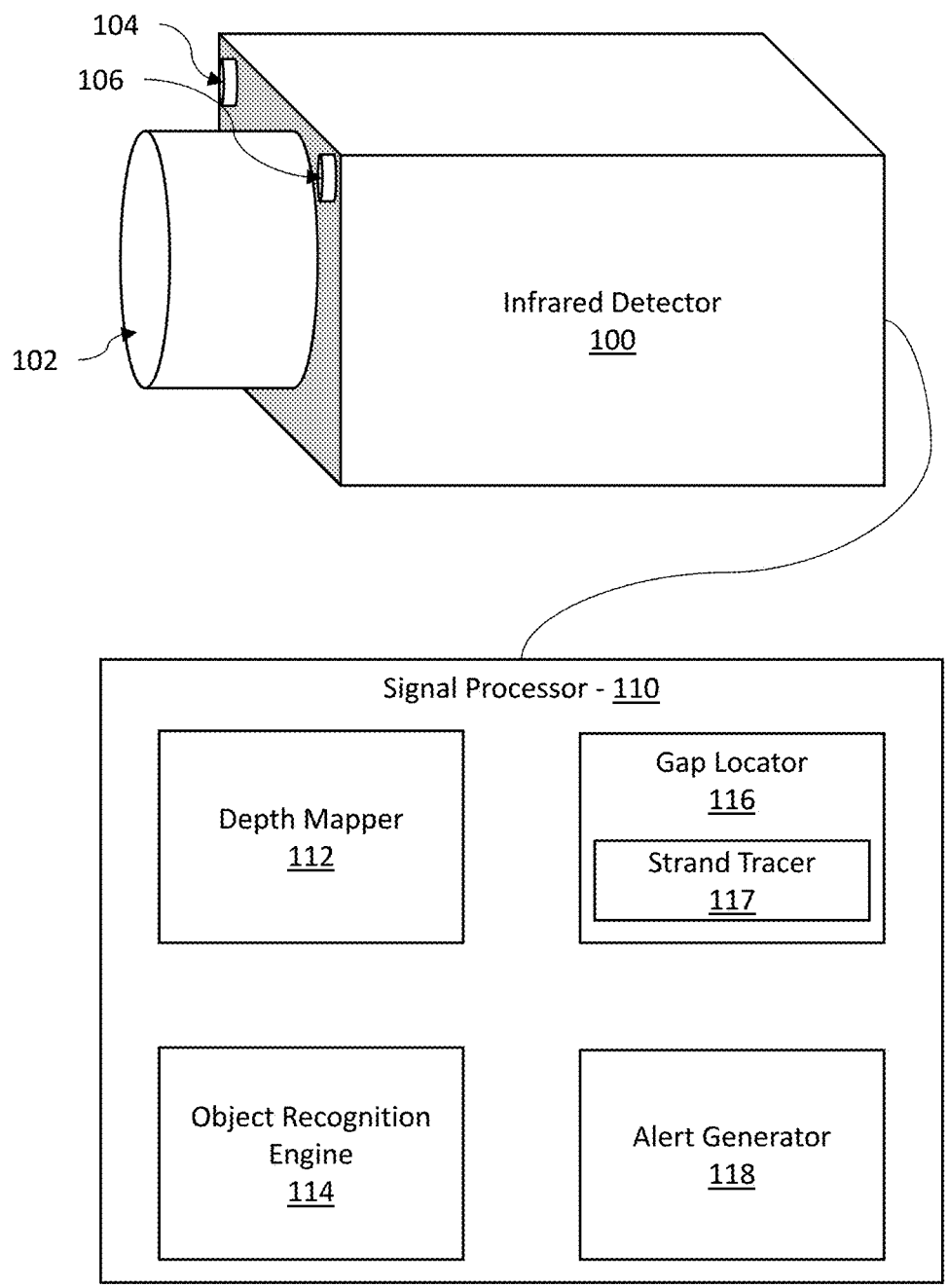
FIG. 4 is a side view showing a netting gap detection device and method, in accordance with an embodiment of the present invention.

Referring now to FIG. 4, a side view of a netting gap detection device and method is shown in accordance with an embodiment of the present invention.

According to an embodiment of the present invention, an infrared detector 100 can include a signal processor 110, a lens 102, an IR beam emitter 104 and a visible beam projector 106. The IR beam emitter 104 emits an IR signal towards a field of view of the lens 102. The IR signal encounters objects within the field of view and the lens 102 collects reflections of the IR signal reflecting off of the objects. The infrared detector 100 can have a resolution sufficient to resolve IR reflections from individual strands of netting, such as, e.g., about 13 megapixels or more of resolution at a distance of 2 meters.

The signal processor 110 can include, e.g., a depth mapper 112 that can be, e.g., a hardware or software module, such as, e.g., a module stored in a memory and executed by a processor. Because the IR beam emitter 104 is offset from the lens 102, a beam of the IR signal that is emitted from the IR emitter 104 and reflected back to lens 102 has an angle between the emitted signal and the reflected signal. Thus, by determining the angle of the reflected signal through the lens 102, the depth mapper 112 can determine a distance of the object reflecting the IR signal. Each reflected IR signal collected by the lens 102 can, therefore, be analyzed to determine a distance of each object reflecting each corresponding reflected IR signal. Each distance measurement can be aggregated into a map of depths across the field of view of the lens 102, thus creating a three-dimensional (3D) representation of the objects in the field of view, such as, e.g., netting and objects in an area bounded by the netting, including, e.g., a bed.

The depth map can be analyzed by an object recognition engine 114. The object recognition engine 114 can include a suitable mechanism for identifying the netting 120, the bed 122, and any other objects in the field of view of the lens 102, such as, e.g., a hardware or software module, including, e.g., a module stored in a memory and executed by a processor. The object recognition engine 114 can take into account size, shape, distance and spectrum signatures of each object. Thus, a fingerprint for each object can be determined according to the object location, shape and the spectrum of the IR signal reflected back to the lens. For example, the object recognition engine 114 can identify netting based on the configuration of strands and holes as well as the spectrum of IR light reflected back by the material of the strands. Individual segments of netting can be identified as separate segments based on distance and the configuration of the strands and holes. The object recognition engine 114 can similarly analyze the IR reflections in the depth map of each of the objects present within the field of view of the lens 102.

Relative positions of multiple segments of netting can then be determined to identify gaps with a gap locator 116. The gap locator 116 can be, e.g., a hardware or software module, such as, e.g., a module stored in a memory and executed by a processor. The gap locator 116 can identify locations of interest in the depth map. The locations of interest can include areas where more than one layer of netting has been identified in a common area projected from a plane parallel to both the x-direction and y-direction, or where no netting exists in an area projected from the plane that is larger than a hole in the netting.

The gap locator 116 assess the netting at each location of interest to identify a gap. Where no netting exists in an area, the gap locator 116 identifies the area is between ends of segment of the netting and located in front of an area to be bounded by the netting. Thus, the gap locator 116 determines whether the location of interest is in a location where netting should be present to prevent mosquito entry into the area to be bounded. If the netting should be present, the gap locator 116 then identifies the location where no netting exists as a x/y gap. The gap locator 116 can then determine a gap centroid of the x/y gap.

The gap locator 116 also assess the netting at a location of interest having multiple layers of netting. Using the depth map, the gap locator 116 determines a difference in depth between a first layer and one or more subsequent layers at the location of interest. Where the difference in depth is greater than a threshold, such as, e.g., a size of a mosquito, the gap locator 116 identifies the location as a depth-wise gap.

To prevent false positives in depth-wise gap identification, the gap locator 116 checks whether the depth-wise gap is the result of separate segments of netting or a wrinkle in a single segment of netting. Thus, a strand tracer 117 selects a netting strand in one layer of netting that traverses the depth-wise gap. The strand tracer 117 traces the strand from a location outside of the location of the depth-wise gap until the strand comes to an end or traverses through the depth-wise gap in the other layer or layers of netting present in the location of the depth-wise gap. A strand that traverses the depth-wise gap in more than one layer indicates that the layers are part of a same segment of netting. Thus, the located depth-wise gap is the result of a fold or wrinkle in the netting, and thus a false positive depth-wise gap. However, if the strand ends before traversing the depth-wise gap in the other layer or layers then the layers are separate segments of netting and the depth-wise gap is a true positive. Thus, the gap locator 116 can accurately determine that a depth-wise gap exists at a location. The gap centroid of the depth-wise gap can then be determined.

An alert generator 118 can then notify a user of each of the gaps present within the field of view of the infrared detector 100. The alert generator 118 can include a communication to a communication device, such as, e.g., a smartphone, tablet, smartwatch, computer, cell phone, or other device. The communication can include, e.g., a text based notification including a warning that a gap exists and the location of the centroid of each gap. Alternatively or in addition, the notification can include an image of the gaps such that the user can easily find the gaps.

Moreover, the alert generator 118 can send a signal to the visible beam projector 106. The signal can include a command to project a beam in visible light towards the identified gap. Thus, the alert generator 118 uses the visible beam projector 106 as a visual alert to a user that facilitates easy discovery of the gaps in the netting.

Figure 5:
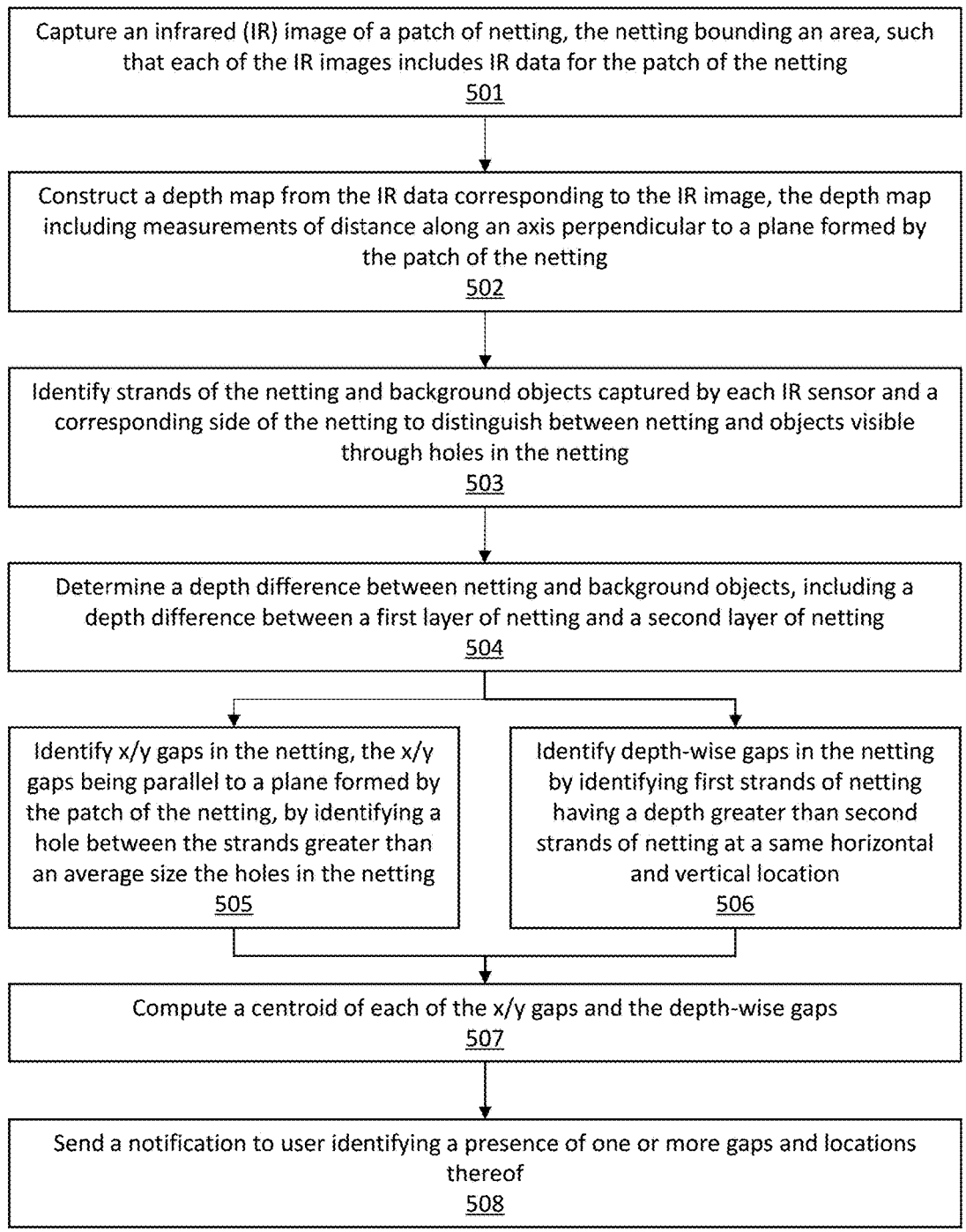
FIG. 5 is a block/flow diagram showing a system/method to detecting and identifying gaps in netting, in accordance with an embodiment of the present invention.

Referring now to FIG. 5, a block/flow diagram of a system/method to detecting and identifying gaps in netting is shown in accordance with an embodiment of the present invention.

At block 501, capture an infrared (IR) image of a patch of netting, the netting bounding an area, such that each of the IR images includes IR data for the patch of the netting.

At block 502, construct a depth map from the IR data corresponding to the IR image, the depth map including measurements of a natural distance of the netting.

At block 503, identify strands of the netting and background objects captured by each IR sensor and a corresponding side of the netting to distinguish between netting and objects visible through holes in the netting.

At block 504, determine a depth difference between netting and background objects, including a depth difference between a first layer of netting and a second layer of netting.

At block 505, identify x/y gaps in the netting, the x/y gaps being parallel to a plane formed by the patch of the netting, by identifying a hole between the strands greater than the size of the smallest mosquito of concern.

At block 506, identify depth-wise gaps in the netting of size greater than that of the smallest mosquito of concern by identifying first strands of netting having a depth greater than second strands of netting at a same horizontal and vertical location.

At block 507, compute a centroid of each of the x/y gaps and the depth-wise gaps.

At block 508, send a notification to user identifying a presence of one or more gaps and locations thereof.

Referring now to FIG. 6, a block/flow diagram of a system/method detecting and identifying depth-wise gaps in netting is shown in accordance with an embodiment of the present invention.

At block 507, depth-wise gaps in the netting are identified by identifying first strands of netting having a depth greater than second strands of netting at a same horizontal and vertical location. According to an embodiment of the present invention, the depth-wise gaps are identified according to blocks 601 and 602.

At block 601, identify a portion of the IR image depicting more than one layer of netting according to at least one strand having a depth measurement different by greater than a threshold from a depth measurement of at least one other strand within a radius of each other in the IR image.

At block 602, determine that the more than one layer are separate segments of netting separated by a depth-wise gap by tracing the one or more strands in the portion from end to end to determine that the at least one strand and the at least one other strand are not connected.

Figure 7:
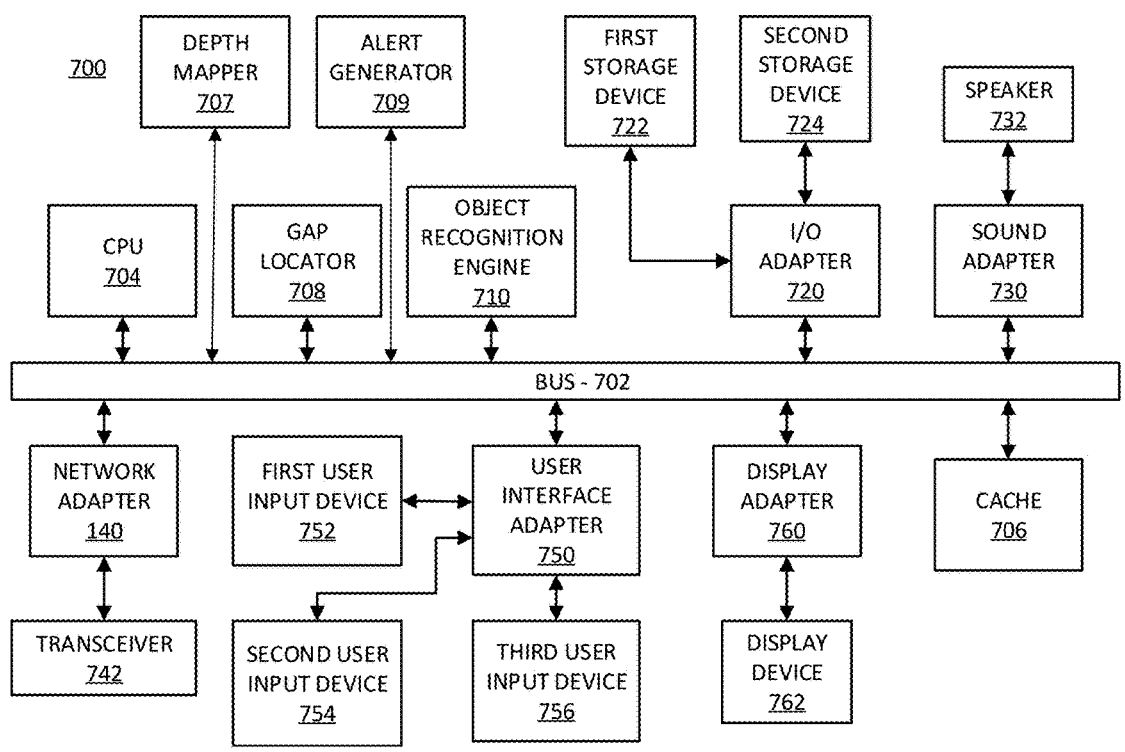
FIG. 7 is a block diagram showing an exemplary processor system for gap detection in netting, in accordance with an embodiment of the present invention.

Referring now to FIG. 7, an exemplary processing system 700 to which the present invention may be applied is shown in accordance with one embodiment. For example, the processing system 700 can be used with or as the signal processor 110 described above. The processing system 700 includes at least one processor (CPU) 704 operatively coupled to other components via a system bus 702.

The processing system 700 includes components for processing an EM signal to determine if gaps are present. A depth mapper 707 is in communication with bus 702 to utilize the EM signal with associated depth measurement to generate a depth map. The depth map can be communicated via the bus 702 to an object recognition engine 710 that is configured to recognize netting in the depth maps, as well as any nearby objects. A gap locator 708 can then determine whether the netting identified in the object recognition engine 710 has any gaps. Identified gaps are communicated to an alert generator 709 via the bus 702. The alert generator 702 can provide commands to other components of the processing system 700 to generate an alert regarding the gaps. Each of the depth mapper 707, object recognition engine 710, gap locator 708 and alert generator 709 can be, e.g., separate processors with associated memory to store models or programs for performing the associated functions. Alternatively, each of the depth mapper 707, object recognition engine 710, gap locator 708 and alert generator 709 can be, e.g., stored in memory devices such as read only memory (ROM) and executed by the CPU 704.

Also, operatively coupled through the system bus 702 are a cache 106, an input/output (I/O) adapter 720, a sound adapter 730, a network adapter 740, a user interface adapter 750, and a display adapter 760.

A first storage device 722 and a second storage device 724 are operatively coupled to system bus 702 by the I/O adapter 720. The storage devices 722 and 724 can be any of a disk storage device (e.g., a magnetic or optical disk storage device), a solid state magnetic device, and so forth. The storage devices 722 and 724 can be the same type of storage device or different types of storage devices.

A speaker 732 is operatively coupled to system bus 702 by the sound adapter 730. A transceiver 742 is operatively coupled to system bus 702 by network adapter 740. A display device 762 is operatively coupled to system bus 702 by display adapter 760. The speaker 732 and/or the display device 762 can generate a user perceptible alert, such as, e.g., an audible alert from the speaker 732 or a visual alert produced by the display device 762.

A first user input device 752, a second user input device 754, and a third user input device 756 are operatively coupled to system bus 702 by user interface adapter 750. The user input devices 752, 754, and 756 can be any of a keyboard, a mouse, a keypad, an image capture device, a motion sensing device, a microphone, a device incorporating the functionality of at least two of the preceding devices, and so forth. Of course, other types of input devices can also be used, while maintaining the spirit of the present invention. The user input devices 752, 754, and 756 can be the same type of user input device or different types of user input devices. The user input devices 752, 754, and 756 are used to input and output information to and from system 700.

Of course, the processing system 700 may also include other elements (not shown), as readily contemplated by one of skill in the art, as well as omit certain elements. For example, various other input devices and/or output devices can be included in processing system 700, depending upon the particular implementation of the same, as readily understood by one of ordinary skill in the art. For example, various types of wireless and/or wired input and/or output devices can be used. Moreover, additional processors, controllers, memories, and so forth, in various configurations can also be utilized as readily appreciated by one of ordinary skill in the art. These and other variations of the processing system 700 are readily contemplated by one of ordinary skill in the art given the teachings of the present invention provided herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as SMALLTALK, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Reference in the specification to "one embodiment" or "an embodiment" of the present invention, as well as other variations thereof, means that a particular feature, structure, characteristic, and so forth described in connection with the embodiment is included in at least one embodiment of the present invention. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

Having described preferred embodiments of a system and method (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

The invention claimed is:

1. A method for detecting gaps in netting, the method comprising:

constructing a map of strands of the netting from electromagnetic signals associated with the netting surrounding an area;
identifying locations of gaps in the netting according to the map; and
alerting a user to the presence and locations of the gaps.

2. The method as recited in claim 1, wherein the electromagnetic signal is an infrared signal.

3. The method as recited in claim 1, further including emitting the electromagnetic signal from an emitter such that a detector detects a reflection of the electromagnetic signal.

4. The method as recited in claim 3, wherein the map includes a depth map constructed by measuring an angle between emitting the electromagnetic signal and detecting the electromagnetic signal.

5. The method as recited in claim 1, wherein identifying locations of the gaps includes:
identifying first strands of netting corresponding to a first layer of netting;
identifying second strands of netting corresponding to a second layer of netting such that the second layer of netting is between the first layer of netting and the area; and
measuring a difference in depth between the first strands of netting and the second strands of netting to determine whether a depth-wise gap exists between the layers.

6. The method as recited in claim 5, wherein determining whether the depth-wise gap exists includes distinguishing between the depth-wise gap and a wrinkle in the netting.

7. The method as recited in claim 6, wherein distinguishing between the depth-wise gap and the wrinkle in the netting includes identifying a wrinkle forming the first layer of netting and the second layer of netting by tracing a strand of netting between the first layer of netting and the second layer of netting.

8. The method as recited in claim 1, wherein identifying the locations of the gaps includes determining a distance in a depth map between an edge of a first segment of netting and an edge of a second segment of netting where no netting exists between each of the edges.

9. The method as recited in claim 1, wherein the location of the gaps include locations where gaps are greater than a size of a mosquito.

10. The method as recited in claim 1, further including projecting a visible beam towards the locations of the gaps.

11. A system for detecting gaps in netting, the system comprising:
an electromagnetic detector that captures an electromagnetic signal from netting surrounding an area;
a signal processor including a memory device and a processor to process the captured electromagnetic signal, including:
a mapper that constructs a map of strands of the netting from the signals
a gap locator that identifies locations of gaps in the netting according to the map of the strands of the netting; and
a notifier that alerts a user to the presence and locations of gaps.

12. The system as recited in claim 11, wherein the electromagnetic detector includes an infrared detector.

13. The system as recited in claim 11, wherein the mapper constructs the map by constructing a depth map from measurements of distance of each of the strands of the netting from the electromagnetic detector.

14. The system as recited in claim 11, further including an electromagnetic emitter that emits the electromagnetic signal such that the electromagnetic detector detects a reflection of the electromagnetic signal.

15. The system as recited in claim 11, wherein the gap locator identifies locations of the gaps including:
identifying first strands of netting corresponding to a first layer of netting;
identifying second strands of netting corresponding to a second layer of netting such that the second layer of netting is between the first layer of netting and the area; and
measuring a difference in depth between the first strands of netting and the second strands of netting to determine whether a depth-wise gap exists between the layers.

16. The system as recited in claim 15, wherein the gap locator includes a strand tracer that identifies whether the depth-wise gap exists by distinguishing between the depth-wise gap and a wrinkle in the netting.

17. The system as recited in claim 11, wherein the gap locator identifies the locations of the gaps includes determining a distance in the map between an edge of a first segment of netting and an edge of a second segment of netting where no netting exists between each of the edges.

18. A non-transitory computer readable storage medium comprising a computer readable program for detecting gaps in netting, wherein the computer readable program when executed on a computer causes the computer to perform the steps of:
constructing a map of strands of the netting from electromagnetic signals associated with the netting surrounding an area;
identifying locations of gaps in the netting according to the map; and
alerting a user of the locations of the gaps.

19. The non-transitory computer readable storage medium comprising the computer readable program as recited in claim 18, wherein identifying locations of the gaps includes:
identifying first strands of netting corresponding to a first layer of netting;
identifying second strands of netting corresponding to a second layer of netting such that the second layer of netting is between the first layer of netting and the area; and
measuring a difference in depth between the first strands of netting and the second strands of netting to determine whether a depth-wise gap exists between the layers.

20. The non-transitory computer readable storage medium comprising the computer readable program as recited in claim 18, wherein identifying the locations of the gaps includes determining a distance in the map between an edge of a first segment of netting and an edge of a second segment of netting where no netting exists between each of the edges.

* * * * *